United States Patent [19]

Michael

[11] Patent Number: 5,468,450
[45] Date of Patent: Nov. 21, 1995

[54] EXPANDING VEHICLE FOR COLORIMETRIC DIAGNOSTIC ASSAYS

[76] Inventor: Richard D. Michael, 7910 Milbury Rd., Baltimore, Md. 21207

[21] Appl. No.: 168,753

[22] Filed: Dec. 16, 1993

[51] Int. Cl.[6] ............................................. G01N 21/00
[52] U.S. Cl. ............................ 422/56; 422/55; 422/57; 435/28; 436/169; 436/805; 119/171; 119/172
[58] Field of Search ........................ 422/55, 56, 57, 422/58, 61; 436/66, 169, 805, 810; 435/28, 805, 810; 119/171, 172, 173

[56] References Cited

U.S. PATENT DOCUMENTS

| | | | |
|---|---|---|---|
| 2,838,377 | 6/1958 | Fonner | 23/230 |
| 3,051,661 | 8/1962 | Collins | 252/408 |
| 3,482,943 | 12/1969 | Csizmas et al. | 422/56 |
| 4,175,923 | 11/1979 | Friend | 436/66 |
| 4,361,648 | 11/1982 | Shuenu-tzong | 435/10 |
| 4,676,950 | 6/1987 | Foster | 422/56 |
| 4,685,420 | 8/1987 | Stuart | 119/1 |
| 4,693,834 | 9/1987 | Hossom | 210/767 |
| 4,971,914 | 11/1990 | Lawrence | 436/66 |
| 5,000,115 | 3/1991 | Hughes | 119/173 |
| 5,071,623 | 12/1991 | Akutsu | 422/56 |
| 5,081,040 | 1/1992 | Patel et al. | 436/66 |
| 5,135,873 | 8/1992 | Patel et al. | 436/180 |
| 5,143,023 | 9/1992 | Kuhns | 119/173 |
| 5,260,031 | 11/1993 | Seymour | 422/101 |
| 5,267,532 | 12/1993 | Franklin et al. | 119/173 |

OTHER PUBLICATIONS

KleanHeart pet products, Fussy Cat Health Monitor Cat litter.
KleanHeart pet products, Fussy Cat D. CatScan™.

*Primary Examiner*—James C. Housel
*Assistant Examiner*—Long V. Le
*Attorney, Agent, or Firm*—Fish & Richardson

[57] ABSTRACT

The invention provides a vehicle for colorimetric assay which expands upon contact with biological fluids. This expansion allows easy visualization of color changes associated with colorimetric assays, particularly when the vehicle is distributed as particles within animal litters.

3 Claims, No Drawings

EXPANDING VEHICLE FOR COLORIMETRIC DIAGNOSTIC ASSAYS

The invention relates to an expanding vehicle for colorimetric diagnostic tests, particularly for use in animal litter products.

BACKGROUND OF THE INVENTION

Quantitative and qualitative colorimetric tests for measuring components of biological fluids are a mainstay of modern medical practice, and are available in different forms, such as dipsticks, treated slides, and reagent solutions in test tubes. The chemical technology of most of these tests is old and in the public domain. For example, reagent tests for the detection of occult blood were developed before the 20th century. Modern colorimetric tests for blood often utilize the same chemical reactions as do the older tests, in which the peroxidate-like activity of hemoglobin catalyzes the oxidation of a variety of leuco dyes (chromogens) to produce a highly distinctive color, thereby indicating the presence of blood.

There are currently several products available for detecting fecal occult blood, incorporating different chromogens and delivery systems. One example is disclosed in U.S. Pat. No. 3,996,006, and is marketed under the trade name "Hemoccult®". U.S. Pat. No. 2,838,377 discloses a delivery system, using the same technology, for use in a toilet bowl. Other colorimetric tests, such as those for blood and urine glucose, pH, protein, leukocyte esterase, ketone bodies, cholesterol, and toxic substances, use different delivery mechanisms.

Certain applications require specialized delivery formats. One such application is in the analysis of various components of domestic and companion animal urine. Analysis of animal urine can be costly, and obtaining a clean specimen is often difficult, particularly with cats. These factors may dissuade pet owners from having urine tests performed, at the expense of timely and appropriate veterinary care for the animals. Detecting blood in animal urine and feces is one of the most frequently required veterinary tests, since the presence of blood in excreta is an early sign of many disease processes, including urinary and intestinal neoplasms, poisoning, trauma, inflammations, infections, and urinary system calculi. In these conditions, early detection and prompt therapy are necessary to expedite successful treatment.

Feline Urological Syndrome (F.U.S.) is a common cause of hematuria (blood in urine) in cats, affecting 21.5% of all male cats and 13.5% of all female cats. Furthermore, many animals with an episode of F.U.S. suffer a recurrence of the disorder. The mortality rate from the condition is over 20%, from uremia, dehydration, shock, and in some cases, from bladder rupture. If initiated early, treatment is usually successful.

SUMMARY OF THE INVENTION

The invention provides a colorimetric diagnostic assay adapted to detect a predetermined characteristic of animal excreta, such as urine or feces. The assay includes a dried and compressed assay vehicle with at least one chromogen on the vehicle, which is inert to the chromogen and which is expandable when wetted by water in the animal excreta. The chromogen is selected to react to only the predetermined characteristic of the excreta to which the assay is directed. The vehicle may be any substance which can be dried and compressed, then rewetted and re-expanded, such as sponge grade cellulose or other resilient or fibrous materials. The vehicular material is characterized by the ability to markedly change volume between the dried, compressed and moistened, expanded states. In a preferred embodiment, a unit volume of the dried and compressed vehicle is expandable, when wetted by the water in the animal excreta, by at least two fold, and most preferably, by at least three fold.

The chromogen may be applied to the surface of, or impregnated into, the sponge grade cellulose. The chromogen may be any which is specific to evaluation of the preselected characteristic of the excreta. In a preferred embodiment, the chromogen is a solution of gum guaiac, such as a solution of between about 0.5 and about 10% gum guaiac, and the characteristic is the presence of hemoglobin in the excreta. In a particularly preferred embodiment, the assay is used to evaluate feline urine for hemoglobin to assess whether the animal has Feline Urological Syndrome (F.U.S.). In other embodiments, the assay may contain at least two chromogens. In some embodiments, a mixture of vehicle particles is provided. One preferred embodiment includes a first assay vehicle and a second assay vehicle, with a first chromogen on the first assay vehicle selected to react to a first predetermined characteristic, and a second chromogen on the second assay vehicle selected to react to a second predetermined characteristic.

The assay vehicle may also include a developer, such as a peroxide developer, applied to the vehicle after the vehicle is wetted by the water in the animal excreta.

The assay may be adapted to be performed in a single step or multiple steps. In a preferred embodiment of a single step assay, the vehicle includes a peroxide developer.

The assay evaluates a predetermined characteristic of animal excreta. The predetermined characteristic can be presence or absence of a substance or quality. The characteristic may be evaluated either qualitatively, based on the presence of a given color or color change, or quantitatively, using a color chart or other means of identifying depth or tone of color as correlated to a quantitative assessment. Examples of characteristics intended to be assessed with the assays of the invention include glucose, pH, protein, blood, hemoglobin, leukocyte esterase, ketone bodies, cholesterol, toxic substances, cysteine, bilirubin, urobilinogen or a hormone such as gonadotrophin, 17-keto steroids, or adrenocorticosteroids.

The assay vehicle may be in pieces of various sizes and shapes. One preferred format is where the dried and compressed vehicle is particulate, with particle diameters of between about 1 and 40 mm. The material may be in the form of sheets, strips, shreds, discs, other decorative shapes such as stars or animal shapes, cubes, spheres, or irregular particles, among other shapes. The assay vehicle may be packaged with directions or color charts for the evaluation of the completed assay.

In another aspect of the invention, the assay vehicle is a component of an animal litter or bedding, for containment or absorption of animal excreta and identification of a predetermined characteristic of the excreta. In this embodiment, the vehicle comprises 1–100% by weight of the litter.

Another aspect of the invention provides a method of producing a colorimetric diagnostic assay adapted to detect a predetermined characteristic of animal excreta. The method includes contacting a dried and compressed assay vehicle with at least one chromogen, the vehicle being inert to the chromogen, the vehicle being expandable by at least two fold when wetted by water in the animal excreta, and the chromogen being selected to react to only the predetermined characteristic of the excreta to which the assay is directed.

The primary object of this invention is to provide an assay vehicle for convenient evaluation of characteristics of animal excreta, without unnecessary manipulation of or trauma to the subject animal. This invention obviates the need for clean urine collection and laboratory urinalysis to diagnose hematuria and other conditions in domestic animals, particularly cats. It is a further object of the invention to provide an assay vehicle suitable for use in an animal litter or bedding. Another object of the invention is to provide an assay vehicle as part of a simple and inexpensive assay system that does not require a laboratory environment or equipment.

DESCRIPTION OF THE PREFERRED EMBODIMENTS

The invention provides an inert expandable vehicle for diagnostic assays The term "inert", as used herein, means that the components of the vehicle must be capable of being commingled with the chromogen and other assay components in a manner such that there is no interaction which would substantially reduce during use the assay's efficacy for evaluating characteristics of animal excreta.

An example of this kind of material is sponge grade cellulose that is available from a variety of sources. To produce a thin compressed sheet, the cellulose may be moistened and then subjected to heat and pressure until dry. When immersed in water, it quickly returns to its pre-compressed dimensions. While in the compressed state this material is readily treated with reagent chemicals dissolved in an appropriate non-aqueous solvent, while still retaining the compressed conformation. In the case of compressed sponge grade cellulose acetone is a suitable solvent. Suitable solvents may be easily chosen for each vehicular composition.

Suitable reagent chromogens can be readily selected for the specific assays desired. For example, glucose may be assayed using glucose oxidase or copper reduction assays, ketone assays may utilize the nitroprusside reaction, bilirubin assays may employ the diazotization method, and urobilinogen assays often use Ehrlich's reagent. Adaptation of these methods to the vehicle of the invention would be readily feasible to those of skill in the art of diagnostic assays. In some applications, the assay would be adaptable for evaluating more than one characteristic at the same time, by providing a mixture of vehicle particles, with different particles carrying different chromogens. For example, one mixture might contain particles for indicating the presence of urinary blood, while other particles in the mixture might indicate urine glucose.

After drying, the sheets of cellulose or other compressed vehicle can be cut to desired sizes and shapes. The sizes and shapes of the material will be selected to provide easy reading of the assay when the vehicle is mixed with animal litter. Vehicle piece size and shape may also be selected for factors such as safety; small particle size may be selected when used for bedding for small animals, or where the animals in question are likely to ingest bedding material.

The resultant assay product would be added to the litter receptacle or mixed into bedding, such as is commonly provided in stables, cages, kennels, and other areas of animal confinement. Where cats are the subject animal this would most likely be the cat litter box containing granular clay or other absorbent litter. When the animal voids in the litter, some of the treated vehicle is contacted by the urine. This would be evidenced by the expansion of the moistened cellulose vehicle, while unwet units would remain compressed. After this contact occurs the necessary developer solution, in this case hydrogen peroxide, is dropped or sprayed onto the pellets to render a color change in the presence of the suspect component. A developer may also be incorporated in the reagent treatment of the compressed cellulose, producing a one step system.

The assay product might be packaged with indications and instructions for use, including interpretive guides such as color charts for evaluating the color change of the wetted, reacted vehicle particles. Instructions might also include indications of when to seek veterinary attention, emergency care measures for a sick animal, how often to use the product, and cautionary warnings about inappropriate ingestion of the product. In other embodiments, the vehicle might be packaged in combination with, packaged alongside, or mixed into an animal litter or bedding product.

The assay is intended for use in evaluating the excreta of an animal subject. "Animal" is intended to encompass any mammalian, avian, or reptilian subject, including nonhuman primates, sheep, horses, cattle, goats, pigs, dogs, cats, rabbits, guinea pigs, hamsters, gerbils, rats, mice, other laboratory animals, domesticated and nondomesticated birds, snakes, turtles, and lizards.

If the urine is positive for the characteristic of interest, a color change occurs. Because of the concomitant expansion upon wetting of the vehicle with animal excreta, little effort or physical contact is required to monitor the reaction. Sensitivity can be adjusted by modifying the reagent concentrations. The colors and color intensities produced will depend on the chromogen or mixture of chromogens used, as well as on the amounts of assayed substances in the excreta.

The protocols below give two examples illustrative of preparation of the assays of the invention.

Protocol for Illustrative One Step Assay

A. Preparation of Chromogen Solution

Dissolve ten (10) grams of tetramethyl benzidine (TMB) in 1000 milliliters of reagent grade acetone at room temperature. Stir solution until completely dissolved. Solution will be a clear pale yellow liquid. Transfer solution to a tightly sealed dark glass container until ready to use in later steps.

B. Preparation of Peroxide Developer

Dissolve 40 grams of polyvinyl pyrrolidone (PVP) in 1000 milliliters of reagent grade methyl alcohol at room temperature. With pipette, slowly add 10 milliliters cumene hydroperoxide to the PVP/alcohol solution. Stir solution until completely dissolved. Transfer solution to a tightly sealed dark glass container until ready to use in later steps.

C. Impregnation of Compressed Cellulosic Vehicle

1. Treatment with chromogen solution.

Transfer chromogen solution into a large glass beaker. Submerge separate compressed cellulose sheets into the beaker individually for two minutes. Transfer treated cellulose sheets to a Buchner or Hirsch funnel or other suction apparatus in order to remove excess chromogen solution. Air dry and protect treated sheets from strong direct light.

2. Treatment with Peroxide Developer

Transfer PVP/cumene hydroperoxide/alcohol solution into a large glass beaker. Submerge separate chromogen impregnated compressed cellulose sheets into the beaker individually for one minute. Transfer re-treated sheets to a Buchner or Hirsch funnel or other suction device in order to again remove all excess reagent. Air dry and protect from strong direct light.

D. Reduction of Cellulosic Sheets to Usable Size

Using a hole puncher to make ¼ inch diameter discs, or strip cutter to make ¼ inch squares, material is easily reduced to discrete units that can be poured into most litters to be used as an intra-litter occult blood assay. When the chromogen-impregnated vehicle is contacted by urine or other animal excreta, it expands. Expansion coupled with color change indicates hematuria.

Protocol for Illustrative Two Step Assay

A. Preparation of Chromogen Solution

Dissolve forty (40) grams of gum guaiac in 1000 milliliters of reagent grade methanol at room temperature. Transfer solution to a tightly sealed dark glass container.

B. Impregnation of Compressed Cellulosic vehicle

Transfer the guaiac/alcohol solution into beaker containing cut squares or punched discs of compressed cellulose sponge vehicle. Use enough of the solution to completely cover cellulosic material. Decant remaining chromogen solution after two minutes of exposure. Transfer treated cellulose units to a Buchner or Hirsch funnel or other suction device in order to remove excess chromogen solution. Air dry. Package in light tight non-metallic container with a pouch containing desiccant, such as silica gel.

C. Exposure and Development of Assay

1. Disperse an adequate number of assay units (sponge particles) into litter pan in order to assure uniform coverage throughout litter. After animal voids check for expansion of assay vehicle units, indicating contact of the units with animal fluids. Using an eye dropper or pipette, place two drops of 3% hydrogen peroxide solution on each expanded unit. Check for color change after thirty seconds. Blue-green tint indicates hematuria.

It should be understood, however, that the foregoing description of the invention is intended merely to be illustrative by way of example only and that other modifications, embodiments, and equivalents may be apparent to those skilled in the art without departing from its spirit.

What is claimed is:

1. An animal litter for adsorption of animal excreta and identification of a predetermined characteristic of the excreta, comprising an animal litter material and particles of a dried and compressed diagnostic assay vehicle, with at least one chromogen in a non-aqueous solvent in the vehicle, the vehicle being inert to the chromogen, the dried and compressed vehicle being expandable by at least three fold when wetted by water in the animal excreta, and the chromogen being selected to react to the predetermined characteristic of the excreta to which the assay is directed.

2. The litter of claim 1, wherein the vehicle comprises 1–100% by weight of the litter.

3. The litter of claim 2, wherein the predetermined characteristic is blood.

\* \* \* \* \*